United States Patent [19]
Cortes et al.

[11] Patent Number: 6,127,576
[45] Date of Patent: *Oct. 3, 2000

[54] AMINOPHENYL KETONE DERIVATIVES AND A METHOD FOR THE PREPARATION THEREOF

[75] Inventors: David A. Cortes, Fairless Hills, Pa.; Kenneth A. M. Kremer, Lawrenceville, N.J.

[73] Assignee: American Cyanamid Company, Madison, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/964,719

[22] Filed: Nov. 5, 1997

Related U.S. Application Data

[60] Provisional application No. 60/034,330, Dec. 20, 1996.

[51] Int. Cl.$^7$ .................................................. C07C 311/08
[52] U.S. Cl. ................................ 564/99; 549/488; 564/91
[58] Field of Search ........................ 564/91, 99; 514/471; 549/488

[56] References Cited

U.S. PATENT DOCUMENTS

| | | | |
|---|---|---|---|
| 4,559,081 | 12/1985 | Van Gemert | 71/93 |
| 4,602,939 | 7/1986 | Van Gemert | 71/92 |
| 4,622,065 | 11/1986 | Van Gemert | 71/93 |
| 4,716,169 | 12/1987 | Heider et al. | 514/299 |
| 5,009,699 | 4/1991 | Brady et al. | 71/92 |
| 5,107,023 | 4/1992 | Brady et al. | 564/305 |
| 5,281,726 | 1/1994 | Cortes | 549/475 |
| 5,362,911 | 11/1994 | Cevasco et al. | 564/305 |
| 5,364,968 | 11/1994 | Burello et al. | 564/416 |
| 5,405,998 | 4/1995 | Cevasco et al. | 564/404 |
| 5,414,136 | 5/1995 | Cortes | 568/306 |
| 5,426,230 | 6/1995 | Douglas et al. | 564/442 |
| 5,492,884 | 2/1996 | Condon et al. | 504/214 |

FOREIGN PATENT DOCUMENTS

| | | | |
|---|---|---|---|
| 0 184 122 | 6/1986 | European Pat. Off. | C07D 251/16 |
| 0 264 467 | 4/1988 | European Pat. Off. | C07D 251/16 |
| 0 463 287 A1 | 1/1992 | European Pat. Off. | C07D 239/52 |
| 0 655 436 A1 | 5/1995 | European Pat. Off. | C07C 221/00 |
| 0 661 276 A1 | 7/1995 | European Pat. Off. | C07D 239/545 |
| 249208 | 9/1987 | Germany | C07C 49/807 |
| 251126 | 11/1987 | Germany | C07C 143/78 |
| 53-132535 | 11/1978 | Japan | C07C 97/10 |
| 2281296 A | 3/1995 | United Kingdom | C07C 221/00 |
| WO 95/29167 A1 | 11/1995 | WIPO | C07D 234/42 |
| WO 95/29902 | 11/1995 | WIPO | C07D 251/16 |

OTHER PUBLICATIONS

W. Speckamp et al., "Dihydroquinolones VI (i)". Tetrahedron Letters 35 3795–3796 (1968).

Speckamp, W. N et al 'Dihydroquinolines. VI. Unusual fragmentation of a heterocyclic ring upon sulfur–ylide treatment' CA 69:105481, 1968.

Sugasawa, T et al 'Bulyrophenone derivatives' CA 90:152001, 1979.

Primary Examiner—Amelia Owens
Attorney, Agent, or Firm—Charles F. Costello, Jr.

[57] ABSTRACT

The present invention provides o-aminophenyl ketone derivatives which are intermediates useful in the manufacture of herbicidal sulfamoyl urea compounds, including the crop selective herbicide 1-{[o-(cyclopropylcarbonyl)phenyl]-sulfamoyl}-3-(4,6-dimethoxy-2-pyrimidinyl)urea. Also provided is a method for the preparation of said intermediates.

16 Claims, No Drawings

AMINOPHENYL KETONE DERIVATIVES AND A METHOD FOR THE PREPARATION THEREOF

This appln. claims benefit of provisional Application No. 60/034,330, filed Dec. 20, 1996.

SUMMARY OF THE INVENTION

The present invention provides o-aminophenyl ketone derivatives of formula I

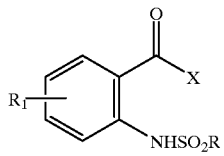

(I)

wherein
R is straight or branched $C_1-C_6$ alkyl or phenyl optionally substituted with $C_1-C_3$ alkyl, $C_1-C_3$ alkoxy, chlorine or bromine;
$R_1$ is hydrogen, cyano, nitro, halogen, formyl, $C_1-C_4$alkyl optionally substituted with one or more halogen, $C_1-C_3$alkoxy, $C_1-C_3$alkylthio, $C_1-C_3$alkylsulfinyl or $C_1-C_3$alkylsulfonyl groups,
  $C_1-C_4$alkoxy optionally substituted with one or more halogen, $C_1-C_3$alkoxy, $C_1-C_3$alkylthio, $C_1-C_3$alkylsufinyl or $C_1-C_3$alkylsulfonyl groups,
  $C_1-C_4$alkylthio optionally substituted with one or more halogen, $C_1-C_3$alkoxy, $C_1-C_3$alkylthio, $C_1-C_3$alkylsufinyl or $C_1-C_3$alkylsulfonyl groups,
  $C_1-C_4$alkylsulfinyl optionally substituted with one or more halogen, $C_1-C_3$alkoxy, $C_1-C_3$alkylthio, $C_1-C_3$alkylsufinyl or $C_1-C_3$alkylsulfonyl groups,
  $C_1-C_4$alkylsulfonyl optionally substituted with one or more halogen, $C_1-C_3$alkoxy, $C_1-C_3$alkylthio, $C_1-C_3$alkylsufinyl or $C_1-C_3$alkylsulfonyl groups,
  $C_1-C_4$alkylcarbonyl optionally substituted with one or more halogen, $C_1-C_3$alkoxy, $C_1-C_3$alkylthio, $C_1-C_3$alkylsufinyl or $C_1-C_3$alkylsulfonyl groups,
  $C_3-C_4$alkoxycarbonyl optionally substituted by one or more halogen or $C_1-C_3$alkoxy groups,
  $di(C_1-C_4$alkyl)amino optionally substituted by one or more halogen or $C_1-C_3$alkoxy groups,
  $di(C_1-C_4$alkyl)aminocarbonyl optionally substituted by one or more halogen or $C_1-C_3$alkoxy groups,
  $di(C_1-C_4$alkyl)aminosulfonyl optionally substituted by one or more halogen or $C_1-C_3$alkoxy groups, or
  a heterocyclic ring having 2 to 6 carbon atoms and 1 to 3 nitrogen, oxygen or sulfur atoms and being optionally substituted on the carbon atoms with one or more halogen, $C_1-C_4$alkyl or $C_1-C_4$haloalkyl groups;
X is $-(CH_2)_3-Y$, cyclopropyl or tetrahydro-2-oxo-3-furoyl; and
Y is chlorine, bromine or hydroxy; or
the acid addition salt thereof.

Compounds of formula I are useful as intermediates in the manufacture of a wide variety of herbicidal sulfamoyl urea derivatives, and in particular, the manufacture of the crop-selective herbicidal agent 1-{[o-(cyclopropylcarbonyl)phenyl]sulfamoyl}-3-(4,6-dimethoxy-2-pyrimidinyl)urea. Also provided is a method for the preparation of said formula I intermediate.

DETAILED DESCRIPTION OF THE INVENTION

The invention provides a compound of formula I

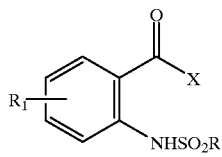

(I)

wherein
R is straight or branched $C_1-C_6$ alkyl or phenyl optionally substituted with $C_1-C_3$ alkyl, $C_1-C_3$ alkoxy, chlorine or bromine;
$R_1$ is hydrogen, cyano, nitro, halogen, formyl, $C_1-C_4$alkyl optionally substituted with one or more halogen, $C_1-C_3$alkoxy, $C_1-C_3$alkylthio, $C_1-C_3$alkylsulfinyl or $C_1-C_3$alkylsulfonyl groups,
  $C_1-C_4$alkoxy optionally substituted with one or more halogen, $C_1-C_3$alkoxy, $C_1-C_3$alkylthio, $C_1-C_3$alkylsufinyl or $C_1-C_3$alkylsulfonyl groups,
  $C_1-C_4$alkylthio optionally substituted with one or more halogen, $C_1-C_3$alkoxy, $C_1-C_3$alkylthio, $C_1-C_3$alkylsufinyl or $C_1-C_3$alkylsulfonyl groups,
  $C_1-C_4$alkylsulfinyl optionally substituted with one or more halogen, $C_1-C_3$alkoxy, $C_1-C_3$alkylthio, $C_1-C_3$alkylsufinyl or $C_1-C_3$alkylsulfonyl groups,
  $C_1-C_4$alkylsulfonyl optionally substituted with one or more halogen, $C_1-C_3$alkoxy, $C_1-C_3$alkylthio, $C_1-C_3$alkylsufinyl or $C_1-C_3$alkylsulfonyl groups,
  $C_1-C_4$alkylcarbonyl optionally substituted with one or more halogen, $C_1-C_3$alkoxy, $C_1-C_3$alkylthio, $C_1-C_3$alkylsufinyl or $C_1-C_3$alkylsulfonyl groups,
  $C_1-C_4$alkoxycarbonyl optionally substituted by one or more halogen or $C_1-C_3$alkoxy groups,
  $di(C_1-C_4$alkyl)amino optionally substituted by one or more halogen or $C_1-C_3$alkoxy groups,
  $di(C_1-C_4$alkyl)aminocarbonyl optionally substituted by one or more halogen or $C_1-C_3$alkoxy groups,
  $di(C_1-C_4$alkyl)aminosulfonyl optionally substituted by one or more halogen or $C_1-C_3$alkoxy groups, or
  a heterocyclic ring having 2 to 6 carbon atoms and 1 to 3 nitrogen, oxygen or sulfur atoms and being optionally substituted on the carbon atoms with one or more halogen, $C_1-C_4$alkyl or $C_1-C_4$haloalkyl groups;
X is $-(CH_2)_3-Y$, cyclopropyl or tetrahydro-2-oxo-3-furoyl; and
Y is chlorine, bromine or hydroxy; or
the acid addition salt thereof.

The invention also provides a process for preparing a compound of formula A

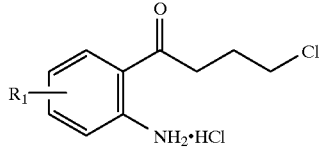

A wherein $R_1$ is as defined in claim 1 which comprises the following steps:

i) reacting a compound of formula B

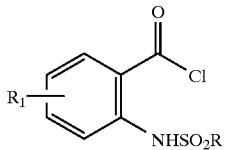

B wherein R and R₁ are as defined in claim 1 with a compound of formula C

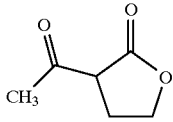

C in the presence of a base and an organic solvent to form a mixture of compounds of formula D and formula E

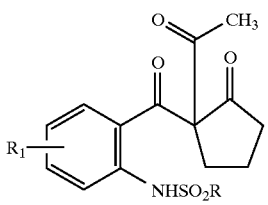

D

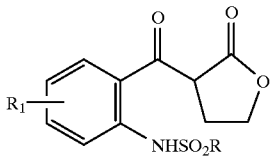

E ii) isolating compound E by hydrolysis or crystallization;

iii) reacting compound E with concentrated HCl in the presence of an organic solvent to form a compound of formula F;

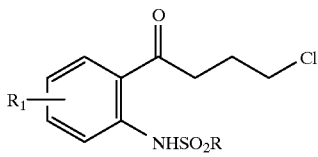

F iv) treating compound F with an aqueous base at an elevated temperature;

v) isolating a compound of formula G;

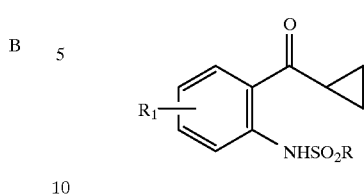

G vi) treating compound G with a strong acid;

vii) isolating a compound of formula H; and

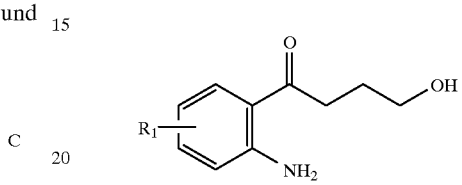

H viii) reacting compound H with HCl to form the compound of formula A.

Compound A wherein $R_1$ is hydrogen, 1-(o-aminophenyl)-4-chloro-1-butanone hydrochloride, is used in the manufacture of the herbicidal intermediate o-(aminophenyl)cyclopropyl ketone. A description of o-(aminophenyl)cyclopropyl ketone and its use in the manufacture of 1-{[o-(cyclopropylcarbonyl)phenyl]-sulfamoyl}-3-(4,6-dimethoxy-2-pyrimidinyl)urea herbicide are found in U.S. Pat. No. 5,009,699. The present invention avoids the explosive o-nitrobenzoyl chloride intermediate of U.S. Pat. No. 5,364,968.

The base used in step 1 may be a magnesium $C_1$–$C_4$ alkoxide, preferably one which is readily available such as magnesium methoxide or magnesium ethoxide. The organic solvent used in step 1 may be an aromatic hydrocarbon or dialkyl ether such as toluene, xylene or tetrahydrofuran. The organic solvent used in step 3 for preparing compound F may be an inert organic solvent such as toluene or xylene and the acid used in step 3 may be a mineral acid such as concentrated HCl. The base used in step 4 for preparing compound G may be an alkali metal hydroxide such as sodium hydroxide or potassium hydroxide. The elevated temperature in step 4 may be any temperature in excess of 25° C., preferably about 90°–130° C. The strong acid used in step 6 for preparing compound H may be sulfuric acid. The acid used for preparing compound A in step 8 may be a mineral acid such as concentrated HCl.

The compounds of the invention may be used to prepare herbicidal sulfamoyl urea compounds (K) by employing the process of the invention to prepare compounds of formula A and converting said formula A compounds to the corresponding o-(aminophenyl)cyclopropyl ketones (J) using conventional methods such as those described in U.S. Pat. No. 5,362,911, and converting said phenyl ketones to the desired sulfamoylurea herbicidal products, preferably the cereal-selective, herbicidal sulfamoyl urea, 1-{[o-(cyclopropylcarbonyl)phenyl]sulfamoyl}-3-(4,6-dimethoxy-2-pyrimidinyl urea. The conversion of the phenyl ketone derivatives to sulfamoylurea herbicides may be accomplished by known processes such as those described in WO 95/29902, EP 661,276, WO 95/29167 and U.S. Pat. No. 5,008,699. The preparation is shown in flow diagram I.

FLOW DIAGRAM I

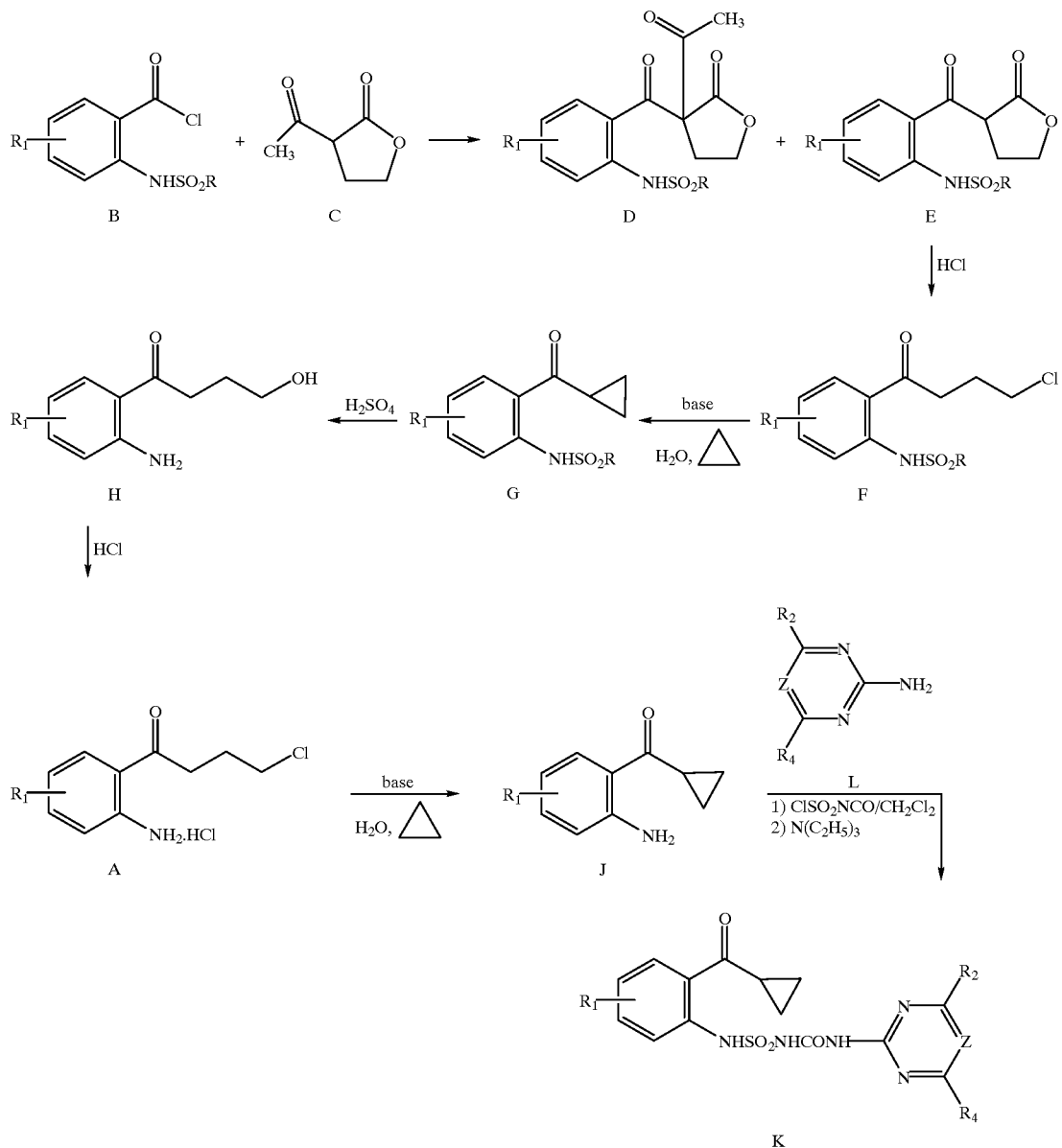

In accordance with the process of the invention, the compound of formula A is prepared as described hereinabove and converted to the o-(aminophenyl)cyclopropyl ketone compound of formula J by conventional dehydrohalogenation techniques and the formula J compound may be reacted with a 2-aminoaryl compound of formula L and chlorosulfonyl isocyanate in the presence of triethylamine and a solvent to give the desired herbicidal sulfamoyl urea of formula K.

The invention is further illustrated in the examples, below, but is not to be deemed limited thereby. The terms NMR and MS designate proton nuclear magnetic resonance and mass spectrometry, respectively.

EXAMPLE 1

Preparation of 2'-(Tetrahydro-2-oxo-3-furoyl)-p-toluenesulfonanilide

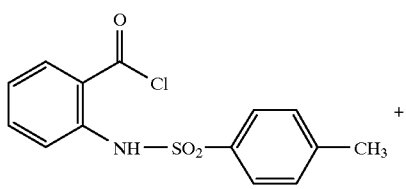

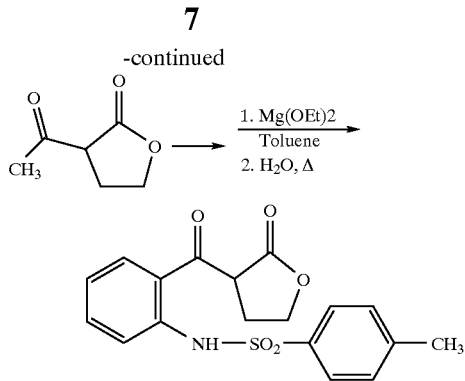

To a mixture of 40 mL of toluene and 2.03 g (178 mmol) of magnesium ethoxide in a flask under nitrogen at 5–10° C. is charged 4.6 g (36 mmol) of 2-acetylbutyrolactone over 2 minutes. The resulting slurry is stirred for 10 minutes at 5–10° C. and for about 1.5 hours at 20° C. The reaction mixture is treated with a solution of 10.0 g (32 mmol) of N-p-tolylsulfonyl anthranoyl chloride in 20 mL of toluene, stirred several hours at ambient temperature and for about 2 hours at 45–50° C. Water (120 mL) is added and the gray slurry is stirred for about 4 hours at 65–70° C. The pH is adjusted to 1 with concentrated sulfuric acid. The phases are separated and the organic layer is filtered to afford 7.6 g of 2'-(tetrahydro-2-oxo-3-furoyl)-p-toluenesulfonanilide. The remaining product is isolated from the organic layer filtrate by concentration in vacuo to give an additional 2.1 g of product for an overall yield of 83% (mp 138–141° C.). The product is identified by NMR and MS analyses.

EXAMPLE 2

Preparation of 2'-(Cyclopropylcarbonyl)-p-toluenesulfonanilide

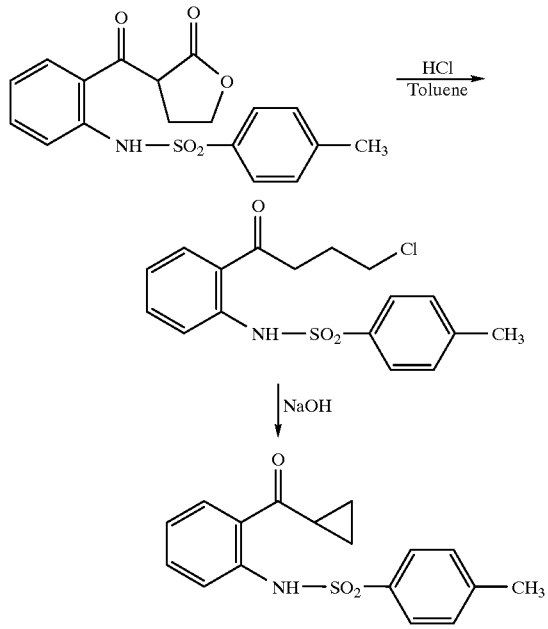

A two phase slurry mixture of 3.56 g (1.0 mmol) of the product from example 1, 25 mL of toluene and 20 mL of 37% HCl is refluxed for about 12 hours, cooled and the resulting slurry is filtered to afford 1.98 g of 4-chloro-1-(2- N-tosylaminophenyl)-1-butanone. The filtrate phases are separated and the aqueous phase is extracted with toluene. The organic phases are combined and concentrated in vacuo to give the remaining 4-chloro-1-(2-N-tosylaminophenyl)-1-butanone product (1.15 g) for an overall yield of 90% (mp 108–113° C.). The product is identified by NMR and MS analyses.

To a solution of 1.62 g (4.6 mmol) of 4-chloro-1-(2-N-tosylaminophenyl)-1-butanone in 10 mL of toluene is charged 17.3 g (28.7 mmol) of 6.6% sodium hydroxide solution. The resulting two phase mixture is refluxed for about 1 hour, cooled and adjusted to pH 1 with concentrated sulfuric acid. The organic layer is separated and concentrated in vacuo to afford 1.50 g of 2'-(cyclopropylcarbonyl)-p-toluenesulfonanilide in 100% yield (mp 92–100° C.). The product is identified by NMR and MS analyses.

EXAMPLE 3

Preparation of 1-(o-Aminophenyl)-4-chloro-1-butanone hydrochloride

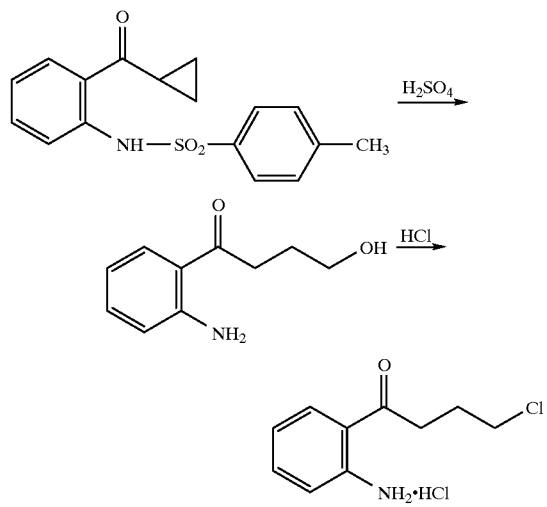

The product of example 2 (1.5 g, 4.7 mmol) is treated with 96% sulfuric acid and heated to 90° C. for 15 minutes. The solution is cooled, adjusted to pH 9 with ammonium hydroxide and extracted with methylene chloride. The combined extracts are concentrated in vacuo to provide 1-(o-aminophenyl)-4-hydroxy-1-butanone (80% yield, mp 58–61° C.). The product is identified by NMR and MS analyses.

A mixture of 9.3 g (5.1 mmol) of 1-(o-aminophenyl)-4-hydroxy-1-butanone, 26 mL of water and 90 mL of 37% HCl is refluxed for about 6.5 hours, cooled and filtered to afford 8.0 g of 1-(o-aminophenyl)-4-chloro-1-butanone hydrochloride. Extraction of the aqueous mother liquor with methylene chloride gives an additional 1.10 g of the title product for an overall yield of 73% (mp 142–145° C.). The product is identified by NMR and MS analyses.

EXAMPLE 4

Preparation of o-Aminophenyl cyclopropyl ketone

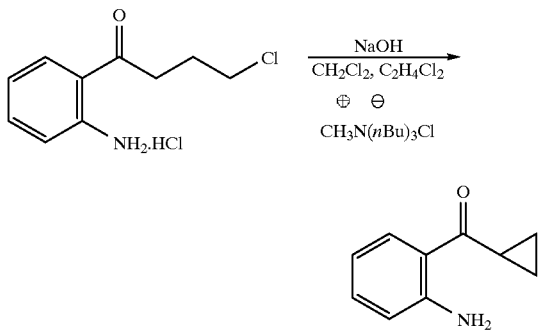

A solution of 0.30 g (1.3 mmol) of 1-(o-aminophenyl)-4-chloro-1-butanone hydrochloride in 3 mL of methylene chloride and 3 mL of ethylene dichloride is treated with 1.2 g (3 mmol) of 10% sodium hydroxide solution and 0.05 g (0.2 mmol) of 75% aqueous methyl tributylammonium chloride and heated to 50° C. for about 5 hours. After cooling to room temperature, the phases are separated. The aqueous layer is extracted with methylene chloride. The combined organic extracts are washed with water and concentrated in vacuo to give 0.14 g (70% yield) of o-aminophenyl cyclopropyl ketone (mp 46–48° C.). The product is identified by NMR and MS analyses.

What is claimed is:

1. A compound of the formula

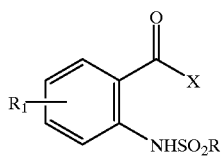

(I)

wherein

R is straight or branched $C_1-C_6$ alkyl or phenyl optionally substituted with $C_1-C_3$ alkyl, $C_1-C_3$ alkoxy, chlorine or bromine;

$R_1$ is hydrogen, cyano, nitro, halogen, formyl, $C_1-C_4$alkyl optionally substituted with one or more halogen, $C_1-C_3$alkoxy, $C_1-C_3$alkylthio, $C_1-C_3$alkylsulfinyl or $C_1-C_3$alkylsulfonyl groups, $C_1-C_4$alkoxy optionally substituted with one or more halogen, $C_1-C_3$alkoxy, $C_1-C_3$alkylthio, $C_1-C_3$alkylsufinyl or $C_1-C_3$alkylsulfonyl groups, $C_1-C_4$alkylthio optionally substituted with one or more halogen, $C_1-C_3$alkoxy, $C_1-C_3$alkylthio, $C_1-C_3$alkylsufinyl or $C_1-C_3$alkylsulfonyl groups, $C_1-C_4$alkylsulfinyl optionally substituted with one or more halogen, $C_1-C_3$alkoxy, $C_1-C_3$alkylthio, $C_1-C_3$alkylsufinyl or $C_1-C_3$alkylsulfonyl groups, $C_1-C_4$alkylsulfonyl optionally substituted with one or more halogen, $C_1-C_3$alkoxy, $C_1-C_3$alkylthio, $C_1-C_3$alkylsufinyl or $C_1-C_3$alkylsulfonyl groups, $C_1-C_4$alkylcarbonyl optionally substituted with one or more halogen, $C_1-C_3$alkoxy, $C_1-C_3$alkylthio, $C_1-C_3$alkylsufinyl or $C_1-C_3$alkylsulfonyl groups, $C_1-C_4$alkoxycarbonyl optionally substituted by one or more halogen or $C_1-C_3$alkoxy groups, di($C_1-C_4$alkyl)amino optionally substituted by one or more halogen or $C_1-C_3$alkoxy groups, di($C_1-C_4$alkyl)aminocarbonyl optionally substituted by one or more halogen or $C_1-C_3$alkoxy groups, di($C_1-C_4$alkyl)aminosulfonyl optionally substituted by one or more halogen or $C_1-C_3$alkoxy groups, or a heterocyclic ring having 2 to 6 carbon atoms and 1 to 3 nitrogen, oxygen or sulfur atoms and being optionally substituted on the carbon atoms with one or more halogen, $C_1-C_4$alkyl or $C_1-C_4$haloalkyl groups;

X is —$(CH_2)_3$—Y, cyclopropyl or tetrahydro-2-oxo-3-furoyl; and

Y is chlorine, bromine or hydroxy; or the acid addition salt thereof, with the proviso that when R is p-tolyl and X is cyclopropyl then $R_1$ is not hydrogen or 4-methoxy; and when R is methyl, X is —$(CH_2)_3$—Y and Y is halogen then $R_1$ is not halogen at the 4 position.

2. The compound according to claim 1 wherein $R_1$ is hydrogen.

3. The compound according to claim 2 wherein R is methyl.

4. The compound according to claim 2 wherein R is p-tolyl.

5. The compound according to claim 2 wherein X is cyclopropyl.

6. The compound according to claim 2 wherein X is —$(CH_2)_3$—Y.

7. The compound according to claim 2 wherein X is tetrahydro-2-oxo-3-furoyl.

8. The compound according to claim 5, wherein R is methyl or p-tolyl.

9. The compound according to claim 6 wherein R is methyl or p-tolyl.

10. The compound according to claim 7 wherein R is methyl or p-tolyl.

11. A process for preparing a compound of formula A

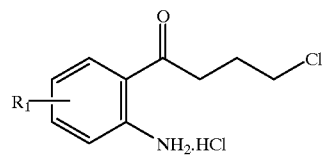

A wherein $R_1$ is as defined in claim 1 which comprises the following steps:

i) reacting a compound of formula B

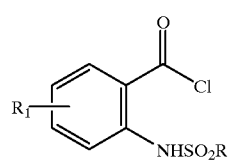

B wherein R and $R_1$ are as defined in claim 1 with a compound of formula C

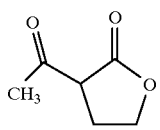
C in the presence of a base and an organic solvent to form a mixture of compounds of formula D and formula E

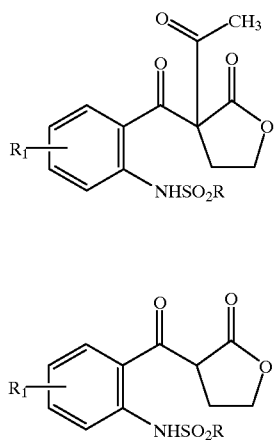

ii) isolating compound E by hydrolysis or crystallization;
iii) reacting compound E with concentrated HCl in the presence of an organic solvent to form a compound of formula F;

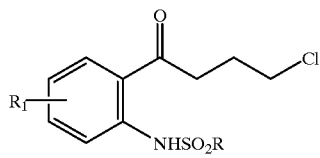
F iv) treating compound F with an aqueous base at an elevated temperature;
v) isolating a compound of formula G;

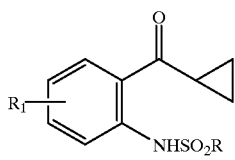
G vi) treating compound G with a strong acid;
vii) isolating a compound of formula H; and

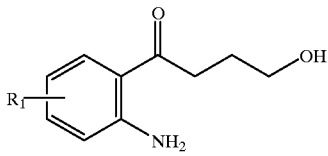
H viii) reacting compound H with HCl to form the compound of formula A.

12. The process according to claim 11 wherein the base in step 1 is magnesium ethoxide and the organic solvent is toluene; the organic solvent in step 3 is toluene; the base in step 5 is NaOH; and the strong acid in step 6 is sulfuric acid.

13. The process according to claim 12 having a compound of formula B wherein $R_1$ is hydrogen.

14. The process according to claim 12 having a compound of formula B wherein R is p-tolyl.

15. The process according to claim 12 having a compound of formula B wherein R is methyl.

16. The process according to claim 13 which further comprises reacting compound A with a base to prepare o-aminophenyl cyclopropyl ketone.

* * * * *

UNITED STATES PATENT AND TRADEMARK OFFICE
CERTIFICATE OF CORRECTION

PATENT NO. : 6,127,576
DATED : October 3, 2000
INVENTOR(S) : D.A. Cortes; K.A. Kremer It is certified that error appears in the above-identified patent and that said Letters Patent is hereby corrected as shown below:

Claims,
Please add claims 17 and 18 below.

17. A process for preparing a sulfamoyl urea compound of formula K

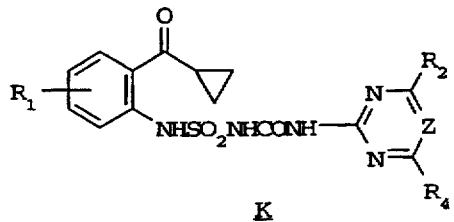

K wherein $R_1$ is as defined in claim 1;
Z is N or $CR_3$;

$R_2$ is hydrogen, halogen, $C_1$-$C_4$alkyl optionally substituted with one or more
    halogen or $C_1$-$C_3$alkoxy groups,
    $C_1$-$C_4$alkoxy optionally substituted with one or more halogen or
        $C_1$-$C_3$alkoxy groups,
    $C_1$-$C_4$alkylthio optionally substituted with one or more halogen or
        $C_1$-$C_3$alkoxy groups,
    $C_1$-$C_4$alkylsulfinyl optionally substituted with one or more halogen or
        $C_1$-$C_3$alkoxy groups,
    $C_1$-$C_4$alkylsulfonyl optionally substituted with one or more halogen or
        $C_1$-$C_3$alkoxy groups, or
    $C_1$-$C_4$alkylamino or di($C_1$-$C_4$alkyl)amino each alkyl group being optionally
        substituted with one or more halogen or $C_1$-$C_3$alkoxy groups;

$R_3$ is hydrogen or halogen; and

UNITED STATES PATENT AND TRADEMARK OFFICE
CERTIFICATE OF CORRECTION

PATENT NO. : 6,127,576
DATED : October 3, 2000
INVENTOR(S) : D.A. Cortes; K.A. Kremer It is certified that error appears in the above-identified patent and that said Letters Patent is hereby corrected as shown below:

R4 is hydrogen, $C_1$-$C_4$alkyl optionally substituted with one or more halogen or
  $C_1$-$C_3$alkoxy groups,
    $C_1$-$C_4$alkoxy optionally substituted with one or more halogen or
      $C_1$-$C_3$alkoxy groups,
    $C_1$-$C_4$alkylthio optionally substituted with one or more halogen or
      $C_1$-$C_3$alkoxy groups,
    $C_1$-$C_4$alkylsulfinyl optionally substituted with one or more halogen or
      $C_1$-$C_3$alkoxy groups,
    $C_1$-$C_4$alkylsulfonyl optionally substituted with one or more halogen or
      $C_1$-$C_3$alkoxy groups, or
$C_1$-$C_4$alkylamino or di($C_1$-$C_4$alkyl)amino each alkyl group being optionally
  substituted with one or more halogen or $C_1$-$C_3$alkoxy group
which comprises:

i)   dehydrohalogenating a compound of formula A

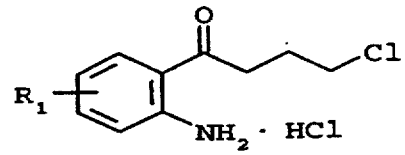

A

UNITED STATES PATENT AND TRADEMARK OFFICE
CERTIFICATE OF CORRECTION

PATENT NO. : 6,127,576
DATED : October 3, 2000
INVENTOR(S) : D.A. Cortes; K.A. Kremer It is certified that error appears in the above-identified patent and that said Letters Patent is hereby corrected as shown below:

prepared by the process of claim 11 to form the o-(aminophenyl)cyclopropyl ketone of formula J

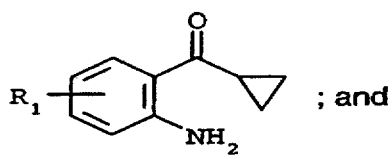

J ii) reacting said o-(aminophenyl)cyclopropyl ketone with a 2-aminoaryl compound of formula L

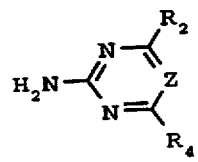

L wherein Z, $R_2$ and $R_3$ and $R_4$ are defined hereinabove
and chlorosulfonyl isocyanate in the presence of triethylamine and a solvent to give the desired sulfamoyl urea compound of formula K.

UNITED STATES PATENT AND TRADEMARK OFFICE
CERTIFICATE OF CORRECTION

PATENT NO.     : 6,127,576
DATED          : October 3, 2000
INVENTOR(S)    : D.A. Cortes; K.A. Kremer It is certified that error appears in the above-identified patent and that said Letters Patent is hereby corrected as shown below:

18.  The process according to claim 17 for preparing a compound of formula K wherein Z is $CR_3$; $R_1$ and $R_3$ are each hydrogen; and $R_2$ and $R_4$ are each methoxy.

Signed and Sealed this

Fifth Day of February, 2002

*Attest:*

JAMES E. ROGAN
*Director of the United States Patent and Trademark Office*

*Attesting Officer*